United States Patent [19]
Jans et al.

[11] Patent Number: 6,153,623
[45] Date of Patent: *Nov. 28, 2000

[54] CISAPRIDE EXTENDED RELEASE

[75] Inventors: Eugene Marie Jozef Jans, Meerhout; Paul Marie Victor Gilis, Beerse, both of Belgium

[73] Assignee: Janssen Pharmaceutic N.V., Belgium

[*] Notice: This patent issued on a continued prosecution application filed under 37 CFR 1.53(d), and is subject to the twenty year patent term provisions of 35 U.S.C. 154(a)(2).

[21] Appl. No.: 08/817,739

[22] PCT Filed: Oct. 25, 1995

[86] PCT No.: PCT/EP95/04198

§ 371 Date: Apr. 23, 1997

§ 102(e) Date: Apr. 23, 1997

[87] PCT Pub. No.: WO96/14070

PCT Pub. Date: May 17, 1996

[30] Foreign Application Priority Data

Nov. 2, 1994 [EP] European Pat. Off. ............... 94203184

[51] Int. Cl.$^7$ ................ A61K 31/445; C07D 211/68
[52] U.S. Cl. ............................ 514/317; 546/194
[58] Field of Search ................ 514/317; 546/194

[56] References Cited

U.S. PATENT DOCUMENTS 5,057,525 10/1991 Van Daele ........................ 514/318

FOREIGN PATENT DOCUMENTS

WO 94/01112  1/1994  European Pat. Off. .
WO A 93 18755  9/1993  WIPO .

OTHER PUBLICATIONS

The Theory and Practice of Industrial Pharmacy; "Sustained Release Dosage Forms"; pp. 452–455 (1986).

*Primary Examiner*—Raymond Henley, III
*Attorney, Agent, or Firm*—Ellen Ciambrone Coletti

[57] ABSTRACT

The present invention concerns extended release formulations comprising cisapride-(L)-tartrate, in particular an oral formulation, the use thereof as a medicine, especially in treating gastrokinetic disorders.

2 Claims, No Drawings

CISAPRIDE EXTENDED RELEASE

CROSS-REFERENCE TO RELATED APPLICATIONS

This application is the national stage of application No. PCT/EP 95/04198, filed on Oct. 25, 1995, which application claims priority from EP 94.203.184.0, filed on Nov. 2, 1994.

The present invention concerns extended release formulations comprising cisapride-(L)-tartrate, in particular for oral administration, the use thereof as a medicine, especially in treating gastro-intestinal disorders.

European Patent No. 0,076,530 discloses the gastroprokinetic agent cisapride and classic compositions thereof. Cisapride has the following structural formula:

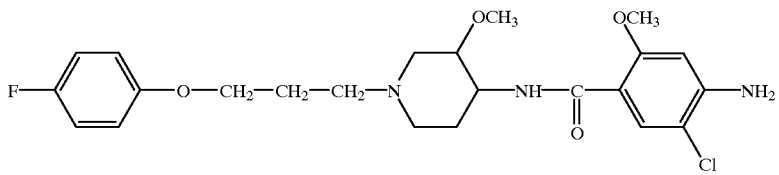

The systematic chemical name of cisapride is cis-4-amino-5-chloro-N-[1-[3-(4-fluorophenoxy)propyl]-3-methoxy-4-piperidinyl]-2-methoxybenzamide. Cisapride is a racemic mixture of two enantiomers. Cisapride has excellent gastro-intestinal motility stimulating properties and is reported to be devoid of antidopaminergic activity. Its utility in a variety of gastro-intestinal disorders has already been reported extensively.

Useful extended release formulations of cisapride for oral administration should release the active ingredient, i.e. cisapride, over a long period of 15 to 24 hours, that is through the whole gastro-intestinal tract with its varying pH values. However, the solubility of cisapride depends very much on the surrounding pH. The solubility of cisapride is the highest in a strongly acidic medium at pH 1 to 2, such as for example in gastric juice. The solubility diminishes rapidly when the pH of the (physiological) medium increases, for example in the intestines. An effective sustained release formulation of cisapride should therefore function not only in highly acidic but also in less acidic or neutral media. Moreover an extended release formulation should release the active ingredient as soon as the formulation is administered and should release the active ingredient in a constant manner, preferably following zero order to first order kinetics. This profile is desired because it provides relief to the patient very soon after administration and overdosing is avoided when administering the formulation for a consecutive time.

A solution to this problem was found in the use of (+)-cis-4-amino-5-chloro-N-[1-[3-(4-fluorophenoxy)propyl]-3-methoxy-4-piperidinyl]-2-methoxybenzamide [R(R*,R*)]-2,3-dihydroxybutanedioate (1:1)—referred to hereinunder as "cisapride-(L)-tartrate"—in a matrix formulation as described hereinafter. Cisapride-(L)-tartrate is the salt of racemic cisapride with (+)-L-tartaric acid and is exemplified in European Patent No. 0,076,530 as compound number 241.

An additional aspect of this invention is the fact that the production process for the present extended release formulations is very simple as is shown in the examples hereinunder. This is in contrast to the production processes known in the art for preparing extended release formulations.

In comparison with other salts of cisapride the salt form with [R(R*,R*)]-2,3-dihydroxybutanedioic acid, i.e. (+)-L-tartaric acid (the natural form of tartaric acid) shows a remarkably good solubility in water. Cisapride being a racemic mixture and L-tartaric acid being one single enantiomer, the resulting salt form is in principle a mixture of two diastereomeric salts: (+)-cisapride-(L)-tartrate and (−)-cisapride-(L)-tartrate.

Unexpectedly, it was shown that the salt cisapride-(L)-tartrate is a mixture of the diastereomers [(3R4S)(2R3R)] and [(3S4R)(2R3R)], that crystallize as a double salt in a 1:1 ratio. (This is confirmed by X-ray.) The (3R4S) and (3S4R) refer to the respective enantiomers of cisapride and the (2R3R) refers to the optically pure L-tartrate.

Unexpectedly, it was found that formulations containing cisapride-(L)-tartrate released cisapride in a racemic form, i.e. equal amounts of (+)-cisapride and (−)-cisapride or in other words the diastereomeric salt forms (+)-cisapride-(L)-tartrate and (−)-cisapride-(L)-tartrate unexpectedly have equal dissolution rates.

Moreover, it was also found that during the preparation of cisapride-(L)-tartrate no enrichment of one of the two diastereomeric salt forms could be detected.

Compositions according to the present invention comprise pharmaceutically acceptable carriers and excipients, such as fillers, e.g. lactose, sucrose, mannitol, maize starch, preferably lactose; lubricants e.g. stearic acid, magnesium stearate, talc or silica or mixtures thereof; preferably a mixture of magnesium stearate, talc and colloidal silicon dioxide (Aerosil®). Also other pharmaceutically acceptable additives such as colorants or flavorings and the like may be present.

The "retard"-effect or "extended release" effect is due to the fact that the cisapride-(L)-tartrate is embedded in a mixture of two viscous polymers. Hence, the formulation comprises a mixture of a highly viscous hydrophilic polymer and a viscous hydrophilic polymer, which releases the active ingredient gradually from the formulation. For the present active ingredient, cisapride-(L)-tartrate, this can conveniently be achieved using a mixture of hydroxypropyl methylcellulose and another viscous cellulose derivative such as, hydroxypropylcellulose, ethylcellulose, hydroxyethylcellulose, hydroxyethyl methylcellulose, methylcellulose, preferably hydroxypropylcellulose.

These two hydrophilic polymers swell when in contact with water, thus creating a porous matrix from which the cisapride can gradually be released. The said polymers themselves also dissolve slowly in the aqueous medium. Consequently, the surface of the formulation is also constantly dissolving and so the aqueous medium can reach the more inward mixture of polymers, that in turn begins swelling and releasing active ingredient thus providing for a continuous release of active ingredient following a zero order to first order kinetics.

The hydroxypropyl methylcellulose used in the above mentioned mixture preferably has a viscosity of about 15,000 mPa.s, e.g. hypromellose 2208.

The hydroxypropylcellulose used in the above mentioned mixture should preferably have a viscosity ranging from 150 to 700 mPa.s, preferably from 200 to 600 mPa.s, e.g. Klucel EF®.

The relative amount of said mixture of viscous hydrophilic cellulose polymers in a formulation ranges preferably between 15% and 35% of the total composition weight. The relative amount of mixture of viscous hydrophilic cellulose polymers correlates with the period during which the active ingredient is released. The lowest limit, i.e. 15%, gives a reasonably extended release period of about 900 minutes. The highest limit, i.e. 35% leads to longer release periods yet still releasing all of the active ingredient present in the formulation. At relative amounts higher than 35% there is expected to be an incomplete release of the active ingredient.

The ratio of the weight hydroxypropyl methylcellulose over weight of the other cellulose polymer ranges from 0.33 to 3. In particular the ratio of the weight of hydroxypropyl methylcellulose over the weight hydroxypropyl cellulose ranges from 0.33 to 3. The preferred ratio is 1, i.e. equal amounts of hydroxypropyl methyl cellulose and hydroxypropylcellulose are present.

The preferred oral formulation of the present invention is a tablet.

Said tablets may have different kinds of shapes, e.g. oblong or right circular. The shape of the tablet influences the release period, because of the fact that different shapes have a different ratio of surface over volume.

A person skilled in the art will appreciate that the volume of the tablet is function of other parameters such as, the actual composition, shape, intended period of release and the intended dose. The exemplified compositions are given for right circular tablets with a diameter of about 11.5 mm diameter and a height of about 5.2 mm.

Said tablets may have lines or break-marks and may bear a symbol or other markings.

Said tablets can optionally be coated with art-known coating compositions. Coated tablets are the preferred formulation in this invention. The above ingredients and ratios apply for the "formulation-core" in general, the "tablet-core" in particular, the compositions of these "formulation-cores" willed be called core-compositions hereinafter.

Suitable coating formulations comprise a film forming polymer such as, for example, hydroxypropyl methylcellulose, e.g. hypromellose 2910 (5 mPa.s); a plasticizer such as, for example, a glycol, e.g. propylene glycol; an opacifier, such as titanium dioxide; a film smoothener, such as talc. Water is added as a solvent.

| Suitable core compositions are: | |
| --- | --- |
| cisapride-(L)-tartrate: | from 2 to 15% by weight |
| filler: | from 50 to 70% by weight |
| hydrophilic polymer mixture: | from 15 to 35% by weight |
| lubricants: | from 0.5% to 10% by weight |
| Interesting core compositions are: | |
| cisapride-(L)-tartrate: | from 5 to 15% by weight |
| filler: | from 50 to 70% by weight |
| hydrophilic polymer mixture: | from 15 to 35% by weight |
| lubricants: | from 0.5% to 10% by weight |
| More interesting core compositions are: | |
| cisapride-(L)-tartrate: | from 8 to 12% by weight |
| filler: | from 55 to 65% by weight |
| hydrophilic polymer mixture: | from 20 to 25% by weight |
| lubricants: | from 2.5% to 8% by weight |
| Particular core compositions are: | |
| cisapride-(L)-tartrate: | about 9% by weight |
| filler: | about 61% by weight |
| hydrophilic polymer mixture: | about 23.5% by weight |
| lubricants: | about 6.5% by weight |
| Preferred core compositions are: | |
| cisapride-(L)-tartrate: | about 9% by weight |
| lactose: | about 61% by weight |
| hydroxypropyl methylcellulose: | from 5.5% to 18% (*) |
| hydroxypropyl cellulose: | from 5.5% to 18% (*) |
| lubricants: | about 6.5% by weight |

(*) the total amount of cellulose derivatives in weight percent being about 23.5%

In view of the gastro-intestinal motility stimulating properties of cisapride, the present invention provides the use of the present formulation as a medicine, in particular in treating gastro-intestinal disorders.

EXPERIMENTAL PART

EXAMPLE 1

To a stirred solution of cis-4-amino-5-chloro-N-[1-[3-(4-fluorophenoxy)propyl]-3-methoxy-4-piperidinyl]-2-methoxybenzamide (4 g) in ethanol (81 ml) was added a solution of [R(R*,R*)]-2,3-dihydroxybutanedioic acid (1.4 g) in ethanol (20 ml) and the product was allowed to crystallize. It was filtered off and dried, yielding 4.8 g (89%) of (+)-cis-4-amino-5-chloro- N-[1-[3-(4-fluorophenoxy) propyl]-3-methoxy -4-piperidinyl]-2-methoxybenzamide [R(R*,R*)]-2,3-dihydroxybutanedioate (1:1), i.e. cisapride-(L)-tatrate. Melting point is 197.1° C. and $[\alpha]_D^{20}$ is 6.7 (c=0.1% methanol).

EXAMPLE 2

Ingredients for the preparation of 1000 tablets (570 mg) of formulation 1:

| Ingredient | amount | % of tablet weight |
| --- | --- | --- |
| cisapride-(L)-tartrate | 52.92 g | 9.3% |
| Lactose | 346.08 g | 60.7% |
| Hydroxypropylmethylcellulose 2208 | 66 g | 11.6% |
| Klucel EF ® | 67.95 g | 11.9% |
| water (*) | 60 g | |
| isopropanol (*) | 140 g | |
| magnesium stearate | 2.85 g | 0.5% |
| Aerosil ® | 5.7 g | 1.0% |
| talc | 28.5 g | 5.0% |

(*)these ingredients are not comprised in the final composition of the tablet.

Preparation

The above mentioned amounts of cisapride-(L)-tartrate, lactose, hydroxypropylmethyl-cellulose, Klucel EF® were sieved over a stainless-steel frame sieve (mesh 0.95 mm) and were mixed in a planetary powder mixer during 5 minutes. The mixture was wetted with isopropanol and water. The wetted mixture was again sieved over a frame sieve (mesh: 1.8 mm). The mixture was dried overnight at a temperature of 45° C. The dried granulate was sieved over a frame sieve (mesh: 0.95 mm). The dried and sieved granulate was mixed with sieved magnesium stearate, Aerosil® and talc in a planetary powder mixer during 5 minutes.

Preparation of Tablets

Using the above described mixture 1000 tablets were compressed.

EXAMPLE 3

Ingredients for the preparation of 1000 tablets (tablets of 570 mg) of formulation 2:

| Ingredient | amount | % of tablet weight |
|---|---|---|
| cisapride-(L)-tartrate | 52.92 g | 9.3% |
| lactose | 346.08 g | 60.7% |
| Hypromellose 2208 | 40 g | 7.0% |
| Klucel EF ® | 93.95 g | 16.5% |
| water (*) | 45 g | |
| isopropanol (*) | 105 g | |
| magnesium stearate | 2.85 g | 0.5% |
| Aerosil ® | 5.7 g | 1.0% |
| talc | 28.5 g | 5.0% |

(*)these ingredients are not comprised in the final composition of the tablet.

Preparation is completely analogous to the preparation as described for formulation 1.

EXAMPLE 4

Ingredients for the preparation of 1000 tablets of formulation

| | |
|---|---|
| cisapride-(L)-tartrate | 52.92 mg |
| lactose monohydrate | 346.08 mg |
| Hypromellose 2208 15000 mPa.s | 66 mg |
| Hydroxypropylcellulose | 67.95 mg |
| water (*) | |
| isopropanol (*) | |
| magnesium stearate | 2.85 mg |
| Aerosil ® | 5.7 mg |
| Talc | 28.5 mg |
| Coating composition | |
| Hypromellose 2910 5 mPa.s | 12 mg |
| propylene glycol | 3 mg |
| titanium dioxide | 3 mg |
| talc | 2 mg |
| water (*) | 120 mg |

Preparation

Cisapride-(L)-tartrate, lactose, Hypromellose and Klucel® are mixed in a high shear mixture-granulator and wetted with a mixture of isopropanol and water. The granulate thus formed is dried by healing in vacuo. After calibrating the dried granulate aerosil, talc and magnesium stearate are added and mixed till a homogeneous mixture is obtained. Biconvex tablets with a diameter of 11.5 mm weighing about 570 mg are compressed.

The tablets are coated in a suitable coating vessel with a coating suspension consisting of hypromellose (5 mPa.s), propyleneglycol, titanium dioxide, talc and water.

We claim:

1. A crystalline form of cisapride-(L)-tartrate wherein the diastereomers [(3R4S)(2R3R)] and [(3S4R)(2R3R)] crystallize as a double salt in a 1:1 ratio.

2. An extended release formulation comprising a compound according to claim 1 and a mixture of hydroxypropylmethyl cellulose and another viscous cellulose polymer, suitable for oral administration wherein the compound is embedded in the mixture.

* * * * *